United States Patent
Erbulut et al.

(10) Patent No.: US 10,265,104 B2
(45) Date of Patent: Apr. 23, 2019

(54) PEDICLE SCREW

(71) Applicants: Deniz Ufuk Erbulut, Istanbul (TR); Suleyman Keles, Izmir (TR); Ali Fahir Ozer, Istanbul (TR)

(72) Inventors: Deniz Ufuk Erbulut, Istanbul (TR); Suleyman Keles, Izmir (TR); Ali Fahir Ozer, Istanbul (TR)

(*) Notice: Subject to any disclaimer, the term of this patent is extended or adjusted under 35 U.S.C. 154(b) by 243 days.

(21) Appl. No.: 15/273,750

(22) Filed: Sep. 23, 2016

(65) Prior Publication Data
US 2017/0079702 A1 Mar. 23, 2017

Related U.S. Application Data

(60) Provisional application No. 62/222,239, filed on Sep. 23, 2015.

(51) Int. Cl.
*A61B 17/70* (2006.01)
*A61B 17/86* (2006.01)

(52) U.S. Cl.
CPC ...... *A61B 17/7046* (2013.01); *A61B 17/7032* (2013.01); *A61B 17/7038* (2013.01); *A61B 17/8605* (2013.01); *A61B 17/8685* (2013.01)

(58) Field of Classification Search
CPC ............ A61B 17/7032; A61B 17/7034; A61B 17/7035; A61B 17/7038; A61B 17/7046; Y10T 403/7018; Y10T 403/7094; Y10T 403/7075; Y10T 403/7077–403/7088
See application file for complete search history.

(56) References Cited

U.S. PATENT DOCUMENTS

| | | | |
|---|---|---|---|
| 2,666,590 A | * | 1/1954 | Pryor .................. B02C 1/14 241/300 |
| 4,946,458 A | | 8/1990 | Harms et al. |
| 5,196,013 A | | 3/1993 | Harms et al. |
| 5,207,678 A | | 5/1993 | Harms et al. |
| 5,443,467 A | | 8/1995 | Biedermann et al. |
| 5,466,237 A | | 11/1995 | Byrd, III et al. |
| 5,474,551 A | | 12/1995 | Finn et al. |
| 5,474,555 A | | 12/1995 | Puno et al. |
| 5,520,690 A | | 5/1996 | Errico et al. |
| 5,531,746 A | | 7/1996 | Errico et al. |
| 5,591,166 A | | 1/1997 | Bernhardt et al. |
| 5,607,426 A | | 3/1997 | Ralph et al. |
| 5,628,740 A | | 5/1997 | Mullane |
| 5,669,911 A | | 9/1997 | Errico et al. |
| 5,672,176 A | | 9/1997 | Biedermann et al. |
| 5,683,392 A | | 11/1997 | Richelsoph et al. |
| 5,690,630 A | | 11/1997 | Errico et al. |
| 5,728,098 A | | 3/1998 | Sherman et al. |
| 5,797,911 A | | 8/1998 | Sherman et al. |
| 5,800,435 A | | 9/1998 | Errico et al. |
| 5,810,819 A | | 9/1998 | Errico et al. |
| 5,863,293 A | | 1/1999 | Richelsoph |

(Continued)

*Primary Examiner* — Matthew J Lawson
*Assistant Examiner* — Amy R Sipp
(74) *Attorney, Agent, or Firm* — MacMillan, Sobanski & Todd, LLC

(57) ABSTRACT

A pedicle screw is provided. The pedicle screw includes a threaded shaft portion and a head portion that is supported on the threaded shaft portion for pivoting movement relative to the threaded shaft portion. A yoke portion is supported on the head portion for linear sliding movement relative to the head portion.

18 Claims, 4 Drawing Sheets

(56) References Cited

U.S. PATENT DOCUMENTS

| | | |
|---|---|---|
| 5,879,350 A | 3/1999 | Sherman et al. |
| 5,891,145 A | 4/1999 | Morrison et al. |
| 5,961,517 A | 10/1999 | Biedermann et al. |
| 5,964,760 A | 10/1999 | Richelsoph |
| 6,053,917 A | 4/2000 | Sherman et al. |
| 6,090,111 A | 7/2000 | Nichols |
| 6,113,601 A | 9/2000 | Tatar |
| 6,132,432 A | 10/2000 | Richelsoph |
| 6,146,383 A | 11/2000 | Studer et al. |
| 6,280,442 B1 | 8/2001 | Barker et al. |
| 6,368,321 B1 | 4/2002 | Jackson |
| 6,471,705 B1 | 10/2002 | Biedermann et al. |
| 6,482,207 B1 | 11/2002 | Errico |
| 6,485,494 B1 | 11/2002 | Haider |
| 6,488,681 B2 | 12/2002 | Martin et al. |
| 6,540,748 B2 | 4/2003 | Lombardo |
| 6,565,565 B1 | 5/2003 | Yuan et al. |
| 6,565,567 B1 | 5/2003 | Haider |
| 6,585,740 B2 | 7/2003 | Schlapfer et al. |
| 6,660,004 B2 | 12/2003 | Barker et al. |
| 6,733,502 B2 | 5/2004 | Altarac et al. |
| 6,858,030 B2 | 2/2005 | Martin et al. |
| 7,141,051 B2 | 11/2006 | Janowski et al. |
| 7,875,065 B2 | 1/2011 | Jackson |
| 8,137,387 B2 | 3/2012 | Garamszegi |
| 8,197,518 B2 | 6/2012 | Hammill, Sr. et al. |
| 8,241,341 B2 | 8/2012 | Walker et al. |
| 8,398,682 B2 | 3/2013 | Jackson et al. |
| 8,657,858 B2 | 2/2014 | Garamszegi et al. |
| 8,790,374 B2 | 7/2014 | Iott et al. |
| 8,852,239 B2 | 10/2014 | Jackson et al. |
| 8,882,809 B2 | 11/2014 | Walker et al. |
| 8,894,691 B2 | 11/2014 | Iott et al. |
| 8,940,024 B2 | 1/2015 | Biedermann et al. |
| 8,998,959 B2 | 4/2015 | Jackson et al. |
| 9,155,568 B2 | 10/2015 | Biedermann et al. |
| 9,179,937 B2 | 11/2015 | Iott et al. |
| 9,198,694 B2 | 12/2015 | Mishra et al. |
| 9,254,151 B2 | 2/2016 | Walker et al. |
| 9,259,254 B2 | 2/2016 | Iott et al. |
| 9,345,519 B1 | 5/2016 | Poirier et al. |
| 2006/0271193 A1* | 11/2006 | Hartmann .......... A61B 17/7032 623/17.11 |
| 2007/0191843 A1* | 8/2007 | Carls .................. A61B 17/7032 606/86 A |
| 2008/0051789 A1* | 2/2008 | Snyder ............... A61B 17/7001 606/86 A |
| 2008/0306552 A1 | 12/2008 | Winslow et al. |
| 2009/0076552 A1 | 3/2009 | Tornier |
| 2009/0182384 A1* | 7/2009 | Wilcox .............. A61B 17/7032 606/305 |
| 2011/0112578 A1* | 5/2011 | Keiser ................ A61B 17/7032 606/264 |
| 2011/0257690 A1 | 10/2011 | Rezach |
| 2012/0016425 A1 | 1/2012 | Shaffrey et al. |
| 2015/0100096 A1* | 4/2015 | Protopsaltis ....... A61B 17/7035 606/306 |
| 2015/0105163 A1* | 4/2015 | Rutkowski ................ F16C 1/08 464/110 |

\* cited by examiner

PEDICLE SCREW

CROSS-REFERENCE TO RELATED APPLICATION

This application claims the benefit of U.S. Provisional Application No. 62/222,239, filed Sep. 23, 2015, the disclosure of which is incorporated herein in its entirety by reference.

BACKGROUND

This invention relates in general to spinal fixation devices. A variety of spinal fixation devices are known for treating scoliosis, spondylolisthesis, degenerative disc disease, vertebra fractures, and other spinal disorders or abnormalities. In many instances, such spinal fixation devices include one or more pedicle screws. A typical pedicle screw includes a threaded shaft portion having a yoke-shaped head portion extending therefrom. The threaded shaft portion is adapted to be secured to a vertebra of the spine, while the head portion is adapted to be connected to a rod or other alignment or immobilization structure.

When used for treatment of spinal disorders or abnormalities, one or more pedicle screws are individually secured to the vertebrae of the spine to provide anchor points that can then be connected together with the rod or other alignment or immobilization structure. However, known pedicle screws do not allow movement of the pedicle screw during flexion and extension of the spine. This may create discomfort for a patient being treated using the pedicle screws.

Therefore, it would be desirable to provide a pedicle screw that allows movement of the pedicle screw during flexion and extension of the spine.

SUMMARY

It should be appreciated that this Summary is provided to introduce a selection of concepts in a simplified form, the concepts being further described below in the Detailed Description. This Summary is not intended to identify key features or essential features of this disclosure, nor is it intended to limit the scope of the invention.

The above objects as well as other objects not specifically enumerated are achieved by a pedicle screw. The pedicle screw includes a threaded shaft portion and a head portion that is supported on the threaded shaft portion for pivoting movement relative to the threaded shaft portion. A yoke portion is supported on the head portion for linear sliding movement relative to the head portion.

There is also provided a pedicle screw including a threaded shaft portion and a head portion attached to the threaded shaft portion. A yoke portion is supported on the head portion for linear sliding movement relative to the head portion.

Various aspects of the pedicle screw will become apparent to those skilled in the art from the following detailed description, when read in light of the accompanying drawings.

DETAILED DESCRIPTION

Figure 1:
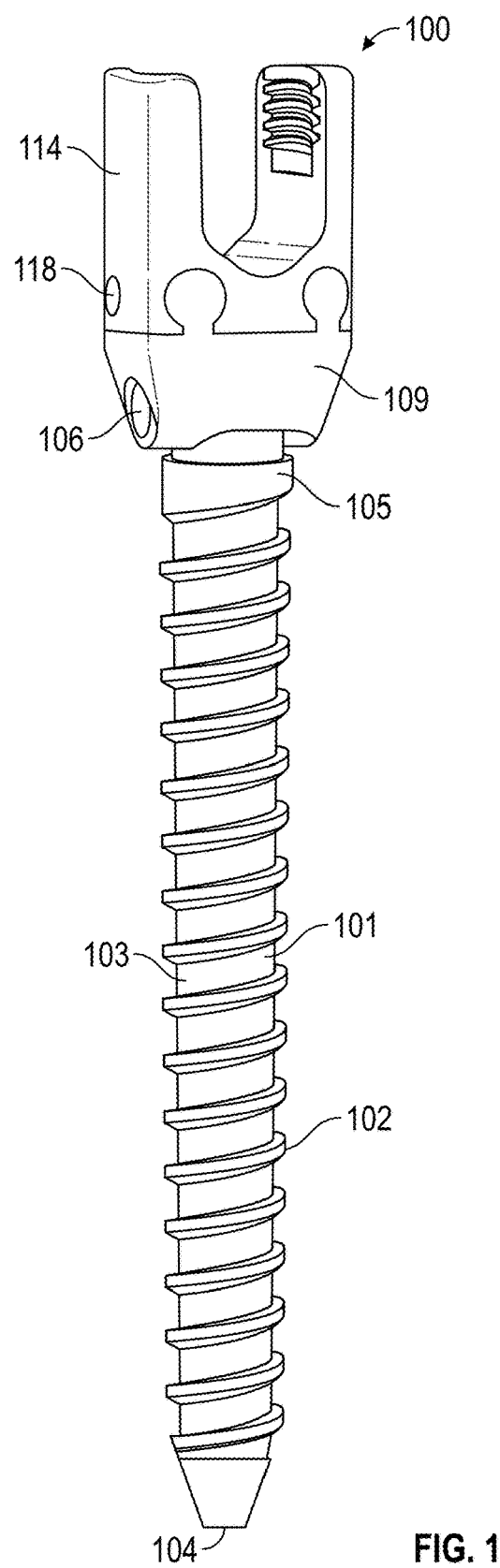
FIG. 1 is a perspective view of a first embodiment of a pedicle screw in accordance with this invention.

The pedicle screw will now be described with occasional reference to specific embodiments. The pedicle screw may, however, be embodied in different forms and should not be construed as limited to the embodiments set forth herein. Rather, these embodiments are provided so that this disclosure will be thorough and complete, and will fully convey the scope of the pedicle screw to those skilled in the art.

Unless otherwise defined, all technical and scientific terms used herein have the same meaning as commonly understood by one of ordinary skill in the art to which the pedicle screw belongs. The terminology used in the description of the pedicle screw herein is for describing particular embodiments only and is not intended to be limiting of the pedicle screw. As used in the description of the pedicle screw and the appended claims, the singular forms "a," "an," and "the" are intended to include the plural forms as well, unless the context clearly indicates otherwise.

Unless otherwise indicated, all numbers expressing quantities of dimensions such as length, width, height, and so forth as used in the specification and claims are to be understood as being modified in all instances by the term "about." Accordingly, unless otherwise indicated, the numerical properties set forth in the specification and claims are approximations that may vary depending on the desired properties sought to be obtained in embodiments of the pedicle screw. Notwithstanding that the numerical ranges and parameters setting forth the broad scope of the pedicle screw are approximations, the numerical values set forth in the specific examples are reported as precisely as possible. Any numerical values, however, inherently contain certain errors necessarily resulting from error found in their respective measurements.

In accordance with the illustrated embodiments, the description and figures disclose a pedicle screw. In certain embodiments, the pedicle screw includes a threaded shaft portion and a head portion that is supported on the shaft portion for pivoting movement relative to the shaft portion. A yoke portion is supported on the head portion for linear sliding movement relative to the head portion.

The term "pedicle screw", as used herein, is defined to mean any fastener attached to a vertebra of the spine, and used as an anchor point for a rod, alignment structure or immobilization structure.

Referring now to the drawings, there is illustrated in FIGS. 1-4 a first embodiment of a pedicle screw, indicated generally at 100, in accordance with this invention. The illustrated pedicle screw 100 may, for example, be used in connection with a posterior dynamic stabilization system or any other alignment or immobilization structure.

Referring again to FIGS. 1-4, the pedicle screw 100 includes a shaft portion 101 having a shaft helical thread 102 provided on an outer surface 103 thereof. In the illustrated embodiment, the shaft helical thread 102 extends from a lower tapered tip 104 of the shaft portion 101 toward an upper end 105 thereof, although such is not required. The shaft helical thread 102 is configured to be secured to a vertebra of a spine (not shown). The shaft helical thread 102 can have any desired thread pitch, thread depth, root diameter and thread diameter sufficient to secure the shaft portion 101 of the pedicle screw 100 to a vertebra of a spine.

Figure 4:
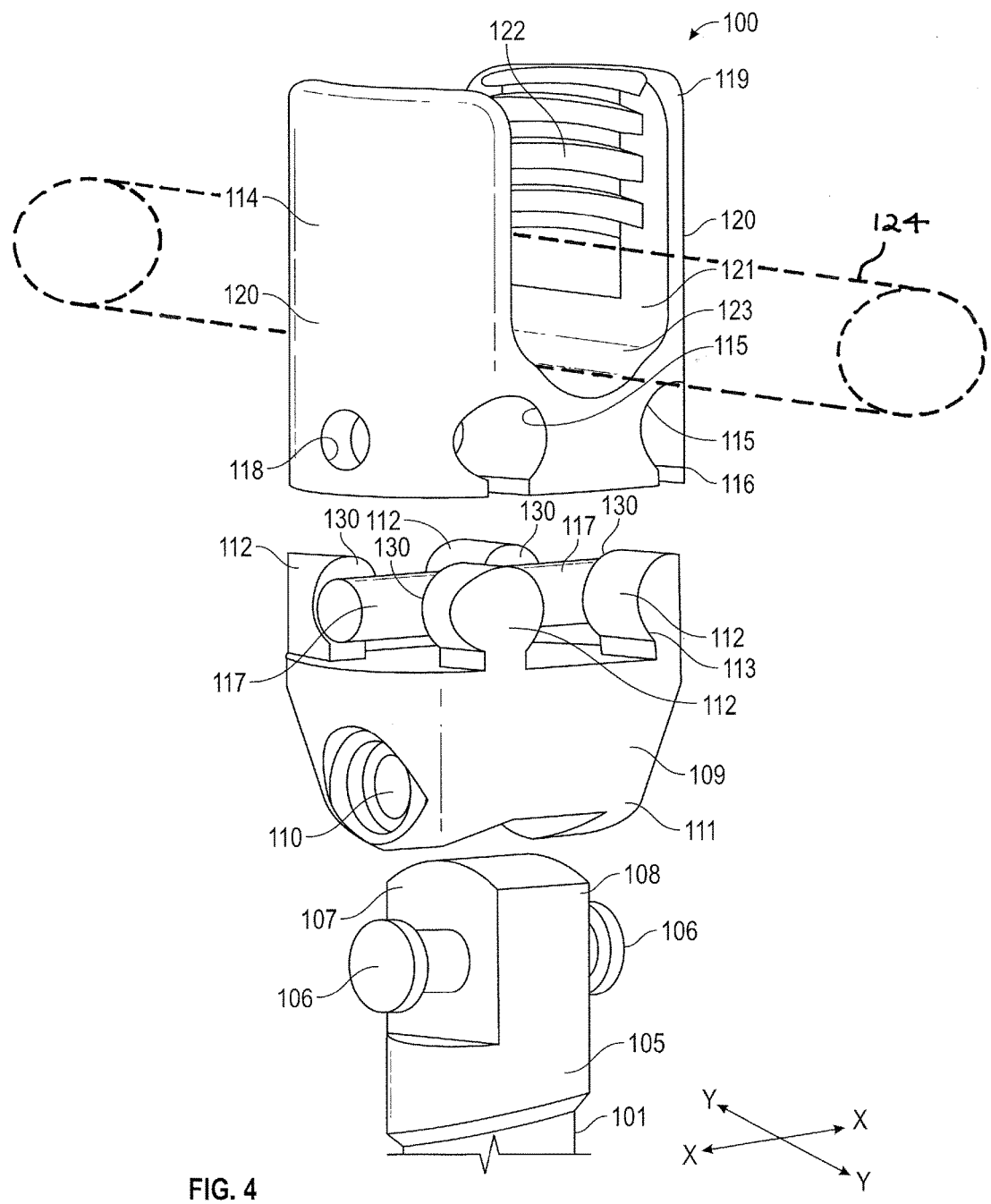
FIG. 4 is an exploded perspective view of a shaft portion, the head portion and the yoke portion of the pedicle screw illustrated in FIG. 1.

Referring now to FIG. 4, the upper end 105 of the shaft portion 101 of the pedicle screw 100 includes a plurality of protrusions 106 provided thereon. In the illustrated embodiment, two of such protrusions 106 extend outwardly from first and second opposed sides 107 and 108, respectively, of the upper end 105 of the shaft portion 101 of the pedicle screw 100, although such is not required.

Referring again to FIGS. 1-4, the pedicle screw 100 also includes a head portion 109 that is supported on the upper end 105 of the shaft portion 101 of the pedicle screw 100. As best shown in FIG. 4, the head portion 109 includes a pair of apertures 110 provided through a lower end, indicated generally at 111, thereof. The apertures 110 are sized and shaped to respectively receive the plurality of protrusions 106 provided on the upper end 105 of the shaft portion 101 of the pedicle screw 100. In the illustrated embodiment, the apertures 110 have a circular cross-sectional shape corresponding to a circular cross-sectional shape of the protrusions 106. However, in other embodiments, the apertures 110 can have other cross-sectional shapes sufficient to receive the cross-sectional shape of the plurality of protrusions 106.

Referring again to FIG. 4, the head portion 109 of the pedicle screw 100 is supported on the upper end 105 of the shaft portion 101 by the protrusions 106 and configured for pivoting movement about an axis X. As a non-limiting example, the head portion 109 of the pedicle screw 100 may be supported on the upper end 105 of the shaft portion 101 for about ten degrees of pivoting movement relative to a sagittal plane. The term "sagittal plane", as used herein, is defined to mean an anatomical plane which divides a body into right and left halves. It should be appreciated that in other embodiments, the pivoting movement relative to a sagittal plane may be more than or less than about ten degrees. In other embodiments, if desired, such pivoting movement of the head portion 109 may be limited to the flexion/extension motion planes. The term "flexion motion plane", as used herein, is defined to mean any angular motions in which two axes of a joint are brought closer together. The term "extension motion planes", as used herein is defined to mean any angular motions in which two axes of a joint are moved further apart.

Referring again to FIG. 4, the head portion 109 of the pedicle screw 100 also includes a plurality of upstanding supports 112 provided on an upper end, indicated generally at 113, thereof. In the illustrated embodiment, a quantity of four of such upstanding supports 112 extend upwardly from the upper end 113 of the head portion 109 of the pedicle screw 100, although such is not required. For example, more than or fewer than a quantity of four of such upstanding supports 112 may extend upwardly, or in other directions, from the upper end 113 of the head portion 109 of the pedicle screw 100.

Figure 2:
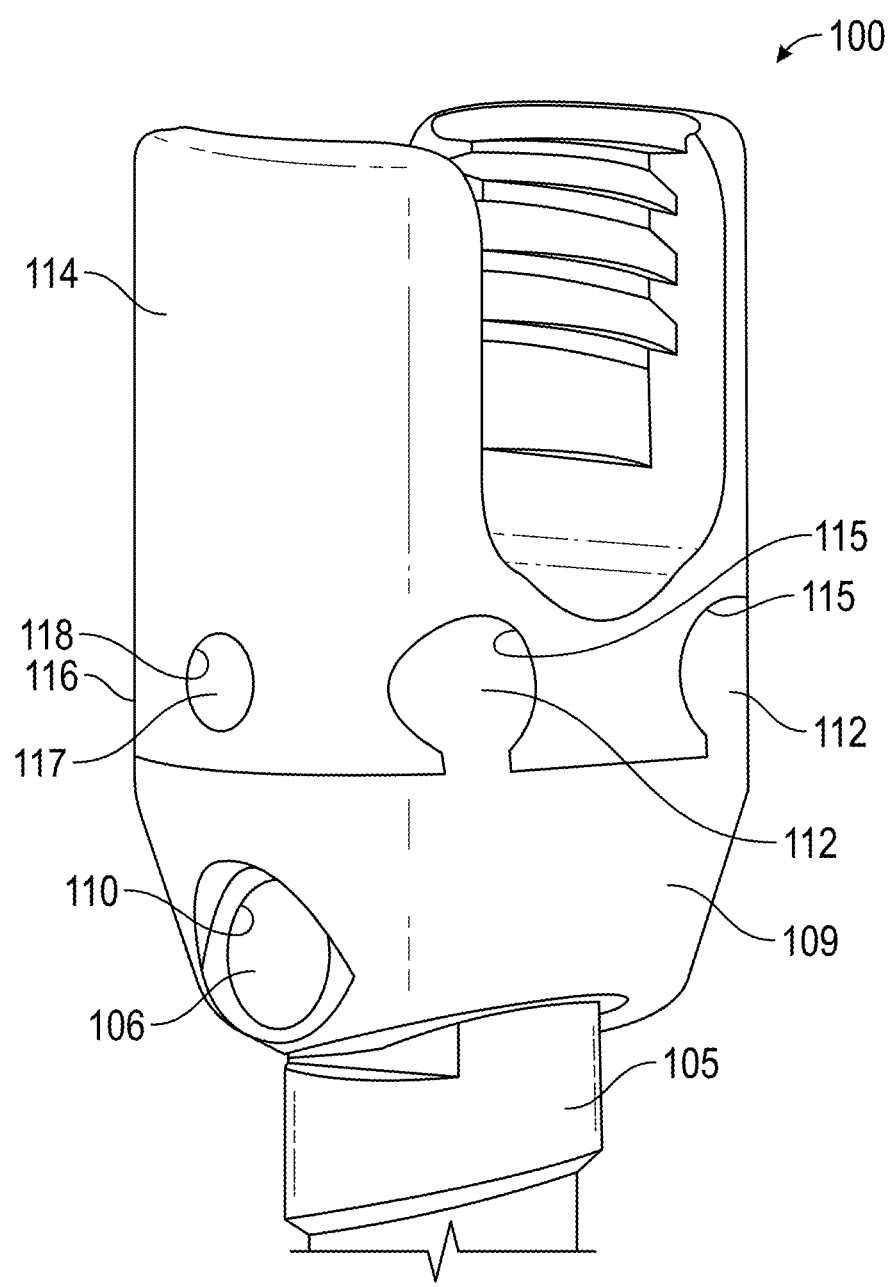
FIG. 2 is an enlarged perspective view of a head portion and a yoke portion of the pedicle screw illustrated in FIG. 1.
Figure 3:
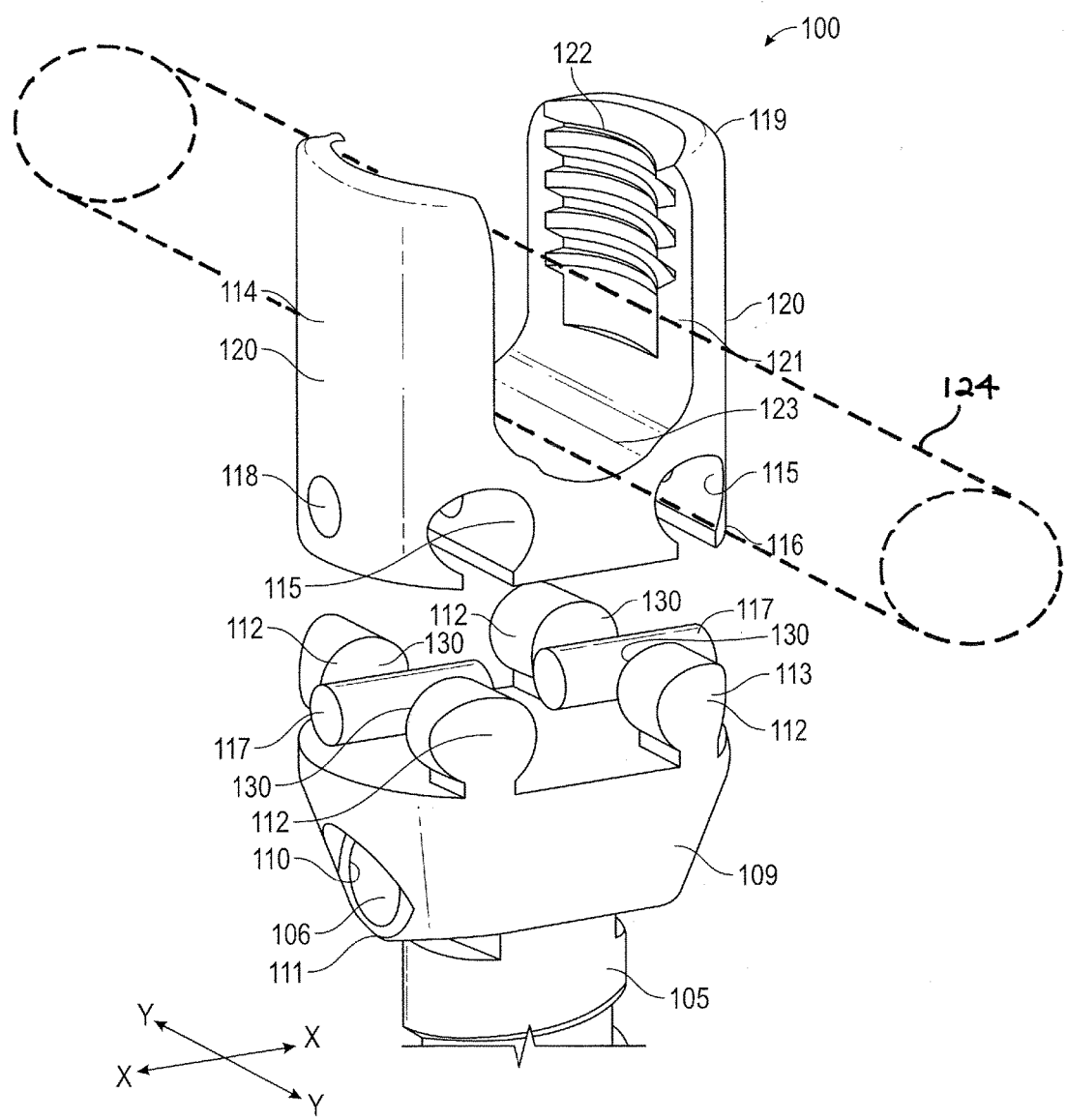
FIG. 3 is a partially exploded perspective view of the head portion and the yoke portion of the pedicle screw illustrated in FIG. 2.

Referring again to FIG. 4, the pedicle screw 100 further includes a yoke portion 114 that is supported on the upper end 113 of the head portion 109 of the pedicle screw 100. As best shown in FIGS. 2, 3, and 4, the yoke portion 114 has a plurality of openings 115 provided in a lower end, indicated generally at 116, thereof. The openings 115 are sized and shaped to respectively receive the upstanding supports 112 provided on the upper end 113 of the head portion 109 of the pedicle screw 100. In the illustrated embodiment, the openings 115 have a circular cross-sectional shape corresponding to a circular cross-sectional shape of the upstanding supports 112. However, in other embodiments, the openings 115 can have other cross-sectional shapes sufficient to receive the cross-sectional shape of the plurality of upstanding supports 112. The openings 115 and the upstanding supports 112 are configured to cooperate with each other such that the yoke portion 114 of the pedicle screw 100 is supported on the upper end 113 of the head portion 109 and the yoke portion 114 is capable of linear sliding movement relative to the head portion 109 along an axis Y.

Referring now to FIGS. 3 and 4, a pair of stop pins 117 are disposed between the upper end 113 of the head portion 109 and the lower end 116 of the yoke portion 114. The stop pins 117 are supported in respective apertures 118 provided in the lower end 116 of the yoke portion 114 (only one aperture 118 is illustrated for purposes of clarity). In the illustrated embodiment, the apertures 118 have a circular cross-sectional shape corresponding to a circular cross-sectional shape of the stop pins 117. However, in other embodiments, the apertures 118 can be other cross-sectional shapes sufficient to receive the cross-sectional shape of the plurality of stop pins 117.

Referring again to FIGS. 3 and 4, the stop pins 117 are disposed between a pair of the upstanding supports 112 provided on the upper end 113 of the head portion 109. When received by the apertures 118, the stop pins 117 are configured to slide with the yoke portion 114 in a linear direction relative to the head portion 109 along an axis Y. As the yoke portion 114 slides, the stop pins 117 are configured to contact interior surfaces 130 of the upstanding supports 112, and effectively limit the distance of the relative linear sliding movement that can occur between the yoke portion 114 and the head portion 109. As a non-limiting example, the stop pins 117 can limit the distance of the relative linear sliding movement that can occur between the yoke portion 114 and the head portion 109 of the pedicle screw 100 to about ±1.0 mm or any other desired amount. In the illustrated embodiment, the interior surfaces 130 of the upstanding supports 112 are substantially flat. However, in other embodiments, the interior surfaces 130 of the upstanding supports 112 can have any desired arrangement, such as the non-limiting examples of an arcuate surface, sufficient to contact the stop pins 117 and limit the distance of the relative linear sliding movement that can occur between the yoke portion 114 and the head portion 109.

Referring again to FIGS. 3 and 4, the yoke portion 114 of the pedicle screw 100 includes an upper end, indicated generally at 119. The upper end 119 includes opposing legs 120. The opposing legs 120 have a generally arcuate cross-sectional shape with interior surfaces 121. The interior surfaces 121 of the opposing legs 120 include a helical thread 122, configured to receive a portion of a fastener (not shown).

Referring again to FIGS. 3 and 4, the opposing legs 120 define a recess 123. The recess 123 is configured to receive a portion of a conventional rod 124 or other alignment or immobilization structure therein. In the embodiment shown in FIGS. 1-4, the recess 123 has the cross-sectional shape of a "U", with the opening of the "U" facing in a substantially vertical direction away from the shaft portion 101. With a portion of the conventional rod 124 or other alignment or immobilization structure positioned in the recess 123, the fastener can be used to secure the rod 124 or other alignment or immobilization structure in the recess 123. In the illustrated embodiment, the fastener is a set screw. In alternate embodiments, the fastener can be other structures, mechanisms or devices, including the non-limiting examples of clips and clamps.

Referring again to FIGS. 3 and 4, the relative linear sliding movement of the yoke portion 114 relative to the head portion 109 may, if desired, be limited to movement in the sagittal plane. As a result, the sliding movement in the sagittal plane will not be affected after connecting the pedicle screw 100 with a rod 124 or other alignment or immobilization structure as described above. The linear sliding function is used to allow a structure using the pedicle screw 100 to move and provide a motion during flexion and extension. Such a structure using the pedicle screw 100 may be, for example, an alignment or immobilization structure.

Although the pedicle screw 100 has been described above and illustrated as including both the head portion 109 and the yoke portion 114, such is not required. Rather, it is within the contemplation of the pedicle screw that the head portion 109 may be supported on the shaft portion 101 in a fixed position relative thereto, while supporting the yoke portion 114 on the head portion 109 for linear sliding movement relative thereto.

While the pedicle screw 100 illustrated in FIGS. 1-4 has been described above as having a head portion that is supported on the threaded shaft portion for pivoting movement relative to the threaded shaft portion and also having a yoke portion that is supported on the head portion for linear sliding movement relative to the head portion, it is within the contemplation of the pedicle screw that the head portion can be attached to the threaded shaft portion such as to eliminate the pivoting movement of the head portion relative to the threaded shaft portion. In this embodiment, the only movement provided by the pedicle screw is the linear sliding movement of the yoke portion relative to the head portion.

The principle and mode of operation of the pedicle screw have been explained and illustrated in its preferred embodiments. However, it must be understood that the pedicle screw may be practiced otherwise than as specifically explained and illustrated without departing from its spirit or scope.

What is claimed is:

1. A dynamic pedicle screw comprising:
   a threaded shaft portion;
   a head portion attached to the threaded shaft portion and configured for pivoting movement relative to the threaded shaft portion;
   a yoke portion that is supported on the head portion for linear sliding movement relative to the head portion and configured to receive an alignment structure; and
   a plurality of rolling stop pins configured to limit the linear sliding movement of the yoke portion relative to the head portion during flexion and extension movements.

2. The dynamic pedicle screw of claim 1, wherein the alignment structure is a rod.

3. The dynamic pedicle screw of claim 1, wherein each of the stop pins is configured to contact a flat interior surface of a support extending from the head portion.

4. The dynamic pedicle screw of claim 1, wherein
   the yoke portion is configured to receive the alignment structure within a recess, and further configured for linear sliding movement relative to the head portion in a direction generally parallel to the alignment structure during flexion and extension movements.

5. The dynamic pedicle screw of claim 4, wherein the recess is defined, in part, by opposing legs forming a portion of the yoke portion.

6. The dynamic pedicle screw of claim 5, wherein the opposing legs have a helical thread formed on a surface of each of the legs forming the recess, and wherein the helical thread is configured to receive a fastener.

7. The dynamic pedicle screw of claim 5, wherein a helical thread is formed on an interior surface of the opposing legs.

8. The dynamic pedicle screw of claim 5, wherein the opposing legs have an arcuate cross-sectional shape.

9. The dynamic pedicle screw of claim 4, wherein the recess has a "U" shape with an opening of the "U" facing in a direction away from the threaded shaft portion.

10. The dynamic pedicle screw of claim 1, wherein the threaded shaft portion includes a shaft helical thread extending from a lower tip of a shaft portion to an upper end of the shaft portion.

11. The dynamic pedicle screw of claim 1, wherein a lower tip of the shaft portion is tapered.

12. The dynamic pedicle screw of claim 1, wherein the threaded shaft portion includes a plurality of protrusions configured to receive the head portion.

13. The dynamic pedicle screw of claim 1, wherein a plurality of protrusions extend from opposing sides of the threaded shaft portion.

14. The dynamic pedicle screw of claim 1, wherein the head portion includes a plurality of supports configured for insertion into a plurality of openings in the yoke portion.

15. The dynamic pedicle screw of claim 14, wherein the plurality of supports have a circular cross-sectional shape.

16. The dynamic pedicle screw of claim 14, wherein the plurality of supports have a flat interior surface configured for contact with the plurality of rolling stop pins.

17. The dynamic pedicle screw of claim 16, wherein each of the rolling stop pins has a circular cross-sectional shape.

18. The dynamic pedicle screw of claim 1, wherein each of the plurality of rolling stop pins are configured to limit the distance of the linear sliding movement of the yoke portion relative to the head portion to about ±1.0 mm.

* * * * *